United States Patent [19]
Larsen

[11] Patent Number: 5,144,224
[45] Date of Patent: Sep. 1, 1992

[54] MILLIMETER WAVE FLOW CYTOMETER

[76] Inventor: Lawrence E. Larsen, 308 Hamilton Ave., Silver Spring, Md. 20901

[21] Appl. No.: 678,245

[22] Filed: Apr. 1, 1991

[51] Int. Cl.⁵ .................. G01N 27/00; G01R 27/04
[52] U.S. Cl. .......................... 324/71.4; 324/632; 324/638; 324/639; 324/642; 324/631; 422/82.11; 422/82.01; 209/576
[58] Field of Search ........... 422/82.01, 82.02, 82.11; 209/571, 576; 324/71.4, 631, 632, 638, 639, 644, 642

[56] References Cited

U.S. PATENT DOCUMENTS

| | | | |
|---|---|---|---|
| 4,507,602 | 3/1985 | Aguirre | 324/639 |
| 4,581,575 | 4/1986 | Osaki | 324/639 |
| 4,866,371 | 9/1989 | De | 324/639 |
| 4,933,075 | 6/1990 | Nordin | 324/629 |
| 4,990,858 | 2/1991 | Garner | 324/639 |

OTHER PUBLICATIONS

Larsen, L. E., Jacobi, J. H., Krey, A. K., IEEE Trans Microwave Theory and Tech 26:581–594, 1978.
Kurokawa, K., IEEE Trans Microwave Theory and Technique 13:194–202, 1965.

Primary Examiner—Kenneth A. Wieder
Assistant Examiner—Jose M. Solis

[57] ABSTRACT

A method and apparatus for millimeter wave flow cytometry of a cell stream hydrodynamically focused in a zone of interaction with a millimeter wave source and complex ratiometric receiver. The cell stream is characterized by complex power wave scattering parameters as a function of frequency, scattering angle and polarization. These parameters train a signal processor to sort specimen cells into one of a plurality of predetermined reference groups in accordance with a minimum number of normal cell types and functional states.

9 Claims, 3 Drawing Sheets

Fig. 3 mmW FLOW CYTOMETER S21 CONFIGURATION

Fig. 4 UNICELLULAR mmW INTERFACE

Fig. 5 UNICELLULAR mmW INTERFACE MULTIFREQUENCY DESIGN

Fig. 6 UNICELLULAR mmW INTERFACE STEPPED DESIGN

Fig. 7
UNICELLULAR mmW INTERFACE
EXPONENTIAL TAPER DESIGN

Fig. 8
UNICELLULAR mmW INTERFACE
FRINGE FIELD COUPLING TO FLOW CHANNEL

MILLIMETER WAVE FLOW CYTOMETER

This application is based on Disclosure #223323 filed on Mar. 30 1989.

U.S. Patents Cited

Bonner, W. A. et al, U.S. Pat. No 3,826,364, *Particle Sorting Method and Apparatus*, 1974.

Coulter, W. H., U.S. Pat. No. 2,656,508, *Means for Counting Particles Suspended in a Fluid*, 1953.

Hansen, W. P. et al, U.S. Pat. No. 4,284,355, *Automated Method for Cell Volume Determination*, 1981.

Harris, W. V., U.S. Pat. No. 4,765,737, *Cell Size Measurements Using Light in Flow Cytometry and Cell Sorting*, 1988.

Jacobi, J. H. and Larsen, L. E., U.S. Pat. No. 4,246,534, *Calibration Methods for Lumped Capacitance Measurement of Complex Permittivity at HF, VHF and UHF Frequencies*, 1981.

Lanier, L., Warner, N. L., U.S. Pat. No 4,607,007, *Differentiation of Natural Killer Cell Subpopulations*, 1986.

Larsen, L. E., and Jacobi, J. H., U.S. Pat. No. 4,240,027, *A Electromagnetic Method for the Noninvasive Analysis of Cell Membrane Physiology and Pharmacology*, 1980.

Leary, J. F. and Todd. P., U.S. Pat. No. 4,263,508, *Pulse Characteristics* 1981.

Lombardo, I. et al, U.S. Pat. No 4,317,520, *Servo System to Control the Spatial Position of Droplet Formation of a Fluid Jet in a Cell Sorting Apparatus*, 1982.

Merrill, J. T., U.S. Pat. No. 4,347,935, *Method and Apparatus for Electrostatically Sorting Biological Cells*, 1982.

Natale, P. J., U.S. Pat. No. 4,336,029, *Methods and Reagents for Quantitative Determination of Reticulocytes and Platelets in Blood*, 1982.

Nozaki, T. et al., U.S. Pat. No. 4,667,830, *Method and Means for Sorting Individual Particles into Containers for Culturing, Cloning or the Like*, 1987.

Ornstein, and Kim, U.S. Pat. No. 4,575,490, *A One Step Method for Sphering and Fixing Whole Blood Erythrocytes*, 1986.

Recktenweld, D. J., U.S. Pat. No. 4,704,891, *Method for Calibrating Flow Cytometers and Other Analysis Instruments*, 1987.

Salzman, G. C. and Kupperman, R. H., U.S. Pat. No. 4,796,995, *Optically Active Particle Distinguishing Apparatus*, 1989.

Schwartz, A., U.S. Pat. No. 4,774,189, *Florescent Calibration Microbeads simulating Stained Cells*, 1988.

Schwartz A., U.S. Pat. No. 4,767,206, *Calibration Method for Flow Cytometry Using Florescent Microbeads and Synthesis Thereof*, 1988.

Shapiro, H. M., U.S. Pat. No. 4,343,782, *Cytological Assay Procedure*, 1982.

Susuki, R. et al, U.S. Pat. No. 4,129,854, *Cell Classification Method*, 1978.

Valett, G., U.S. Pat. No. 4,751,188, *Method for Simultaneous Quantitative Determination of Cells and Reagent Therefor*, 1988.

Other References Cited

Herzenberger, L. A., Sweet, R. G., Herzenberger, Leonore, A., Fluorescent activated cell sorting, *Scientific American*, 234(3) 108, 76.

Hoffman, R. K., *Handbook of Microwave Integrated Circuits*, Artech House, Boston, 1987.

Kachel and Menke, Hydrodynamic properties of flow cytometric instruments, pp 41–59 in Melamed et al, *Flow Cytometry and Sorting*, Wiley, N.Y., 1979.

Larsen, L. E., Jacobi, J. H., Krey, A. K., Preliminary observations with an electromagnetic method for the noninvasive analysis of cell suspension physiology and induced pathophysiology, *IEEE Trans Microwave Theory and Tech*, MTT:26:581–594, 1978.

Nilsson, N. J., *Learning Machines*, Mc Graw Hill, N.Y., 1966.

Melamed, M. R., Mullaney, P. F., Mendelsohn, M. L., *Flow Cytometry and Sorting*, John Wiley and Sons, N.Y., 1979.

Ulriksson, B., A time domain reflectometer using a semiautomatic network analyzer and the fast Fourier transform, *IEEE Trans Microwave Theory and Tech*, MTT29(@):172–174, 1981.

Young, L,, Stepped-impedance transformers and filter prototypes, *IEEE Trans Microwave Theory and Tech*, MTT10(5):339–359, 1962.

AREA OF THE INVENTION

Heretofore, flow cytometers have interrogated cells suspended single file in electrolyte solutions by means of either electrical impedance, so-called resistance pulse, or by optical measurements, for example, scattering measurements or activation of a fluorescent tag. Resistance pulse measurements employ carrier frequencies from DC up to the HF band. Optical scattering and/or fluorescence activation generally employ photopic light.

Resistance pulse methods [Coulter, 1953] have the advantage of simplicity and speed of sample preparation, the paucity of physiologic insight is a serious deficiency. For example, cell viability determination is not possible with resistance pulse methods [Herzenberger et al, 1976]. Cell size is a major determinant of the output signal from resistance pulse techniques. The interaction zone is generally a small orifice across which an electric field is maintained. Cell detection depends upon disruption of the bulk impedance therein as the cell passes through the orifice to displace an equal volume of electrolyte under hydrodynamic focusing to center the cell in the orifice.

Optical methods may involve narrow angle as well as forward scatter along with various vital stains that often include fluorescent tags [Melamed et al, 1979]. Fluorescent methods often employ scattered light in combination with fluorescent activation. Various fluorescent stains may be attached to specific (e.g antibody/antigen pairing) or nonspecific ligands during an incubation period prior to flow cytometry. These fluorescent tags are activated by light pulses gated by auxiliary scattered light signals. Although photopic light scattering involves little sample preparation, physiologic information is often obscured by the fact that cell contents, especially organelles, are Mei (resonant) scatters. Thus, the optical scattering cross section varies rapidly with minor variations in wavelength, polarization, and the diameter of the scattering organelles. Antibodies with fluorescent tags offer great sensitivity, but the cost and complication of sample preparation limit the cost effectiveness of these methods.

The instant invention uses millimeter wave scattering parameter analysis (monostatic one part well as bistatic two part) for carrier frequencies in the range 30 to 300 GHz. Sample preparation is comparable to that of resistance pulse sizing methods, i.e. no incubation or staining is necessary; but physiological insight is improved due to the difference in dielectric constitutive parameters that are accessed in the millimeter wave band as opposed to the bulk cellular impedance properties accessed by pulse resistance techniques where carrier frequencies are lower by a factor of $10^6$ to $10^9$. This benefit is especially important with respect to the cell membrane and biophysical processes thereof with characteristic frequencies in the $10^{10}$ Hz frequency range. The quantum energy associated therewith matches work functions in the cell that correspond to weak inter- and intra-molecular forces rather than bulk impedance. Frequency dependant dielectric properties in the millimeter wave region are generally in the form of relaxation. Size dependant scattering is in the Rayleigh region. Thus, the scattering cross section as a function of frequency is a smooth, monotonic 4th power function of the diameter without the rapid oscillations characteristic of the Mei region. Scattering is generally vector, i.e. polarization dependant, for Rayleigh scatters.

Size dependant scattering at photopic frequencies is in the Mei region for cell organelles and in the optical region for complete cells. The former has vector components, but the latter is generally scalar in nature, i.e weakly polarization dependant scattering cross section as a function of frequency. Frequency dependant dielectric properties are generally in the form resonance. Cell function accessed by stains, whether chromophore or fluorescent, depend upon electron interaction at characteristic frequencies in the terahertz region, i.e. a factor of $10^3$ to $10^4$ high carrier frequency than the instant invention where lower energy work functions such as Van der Wals forces associated with tertiary conformational states within or between biopolymers are addressed. These are of great importance for cell surface state, cell membrane transduction, and second messenger signaling in cell physiology. Light, on the other hand, addresses higher energy work functions associated with the primary and secondary states of biomolecules through interaction with outer shell electrons, vis a vis chemical bonds of chromophores, for example. The interaction zone where optical interrogation takes place is a transparent channel where incident, scattered and emitted light are related to the cell in a fluid sheath.

The technology of the flow system to produce the cell stream, droplet formation, and cell sorting based on measurements of the cell stream are not substantially different from prior art in that hydrodynamic focusing constrains the cells to the center of an interaction region where the cells pass single file with a surrounding sheath of electrolyte through the interaction zone [Bonner, U.S. Pat. No. 3,826,364] and will not be discussed in detail here. The individual cells can exist in air after a nozzle converts the cell stream into air borne droplets. Once in air, the droplets are sorted into collection vessels on the basis of cytometric measurements. High speed logic controls voltages applied to electrostatic deflection plates which act on the droplets after suitable time delays to account for transport from the interaction zone to the nozzle. Nozaki et al [U.S. Pat. No. 4,667,830] improve upon those methods by adapting the apparatus for individual sorting by preventing droplet charging for a predetermined and resettable interval. Another improvement is the Merril patent [U.S. Pat. No. 4,347,935] where droplet-to-droplet distance was used in combination with sensor location along the stream to prevent charging of droplets not in the selection region. Still another example of improvement to cell sorting strategies is the Lombardo et al patent [U.S. Pat. No. 4,317,520] where scattered light was used to indicate droplet formation. Time of flight combining small angle scattering and florescence has been disclosed as a method of cell sizing and sorting by Harris [U.S. Pat. No. 4,765,737].

Many U.S. patents issued for florescent activated flow cytometry deal with calibration standards for florescent methods and serve to underline the operational difficulties that attend that method. These include, for example, Schwartz, [U.S. Pat. No. 4,774,189 and U.S. Pat. No. 4,767,206], Recktenweld, [U.S. Pat. No. 4,704.891], Shapiro, [U.S. Pat. No. 4,343,782], Natale, [U.S. Pat. No. 4,336,029] and Valet, [U.S. Pat. No.4,751,188]. In one case, Susuki et al, [U.S. Pat. No. 4,129,854], a typical cell was selected to set windows and filters for video processing. Lanier and Warner, [U.S. Pat. No. 607,007] used a selected subpopulation of natural killer cells in a similar way to calibrate via fluorochrome labels.

Others deal with improved methods for cell sizing. Ornstein and Kim, [U.S. Pat. No. 4,575,490], add a method of sphering erythrocytes prior to sizing in order to circumvent problems with cell orientation and asymmetry. Hansen [U.S. Pat. No. 4,284,355], used florescent volume exclusion as a means to estimate cell size. Leary and Todd [U.S. Pat. No. 4,263,508] used pulse edge signal processing to improve cell size measurements. Polarization dependant light scattering was disclosed in a recent patent [Salzman and Kupperman, U.S. Pat. No. 4,796,995]. This described a bistatic optical system for circular and linear birefringence.

The instant invention differs from the prior art in that the frequency of the electromagnetic wave is 4 to 6 orders of magnitude lower than the optical (i.e. photopic) techniques and 3 to 5 orders of magnitude higher in frequency than prior electrical methods. The methods and apparatus for signal generation, detection and interaction with the cell stream is totally different from prior art. These topics, especially the last two, are the substance of this application for letters patent.

The advantage of millimeter wave frequency interrogation of cell streams are 1) the specified photon energy accesses work functions in the cell that correspond to weak inter- and intra-molecular forces associated with tertiary conformational states rather than the secondary structure associated with the outer electron states addressed by photopic light or the bulk impedance and volume exclusion estimated by resistance pulse technique; 2) the specified wavelength of the instant invention interacts with cells and cell components as Rayleigh scatters rather than Mei or optical scattering obtained with photopic light thus retaining a smooth and non-oscillatory variation in scattering cross section with respect to frequency; 3) the frequency dependant dielectric properties are in the form of relaxation not the resonant processes associated with light; 4) the stains, fluorescent tags, antibody production and incubation typical of optical techniques are avoided to simplify sample preparation and increase cost effectiveness, most especially for screening applications where early disease detection is paramount.

SUMMARY OF THE INVENTION

The instant invention uses millimeter wave scattering parameter analysis (monostatic as well as bistatic) in the range 30 to 300 GHz to interrogate cells suspended in a hydrodynamically focused flow system. Millimeter wave scattering parameter analysis combines the ease of sample preparation characteristic of electrical methods but with improved physiological insight characteristic of dielectric analysis by vector network analysis as a function of frequency, polarization, and scattering angle; but with neither the problems of Mei scattering nor the use of stains that limit optical methods.

BRIEF DESCRIPTION OF THE DRAWINGS

FIG. 1 is a functional block diagram of the system. It is comprised of four subsystems: the millimetric wave dielectric spectrometer, 100; the unicellular interface, 200, to the cell stream; the means for production of the cell stream, 300; and the cell sorter, 400, applied to the cell stream, after conversion to droplets in air, on the basis of logic applied to the measurements made on the cell stream via 100 and 200 in combination.

FIGS. 2 & 3 are functional block diagrams.

FIGS. 4, 5, 6, 7, and 8 describe the cellular interface. FIG. 4 and 5 are overall elevation and plan views, respectively, of the cellular interface, 200. The cellular interface provides for operant connection to the spectrometer, 100, via a microstrip line launcher(s) shown, for example, with 2.4 mm coaxial connectors suitable for the band 26 to 50 GHz. Similar launchers exist for rectangular waveguide feeds, as is known to those skilled in the art. Interaction with the cell stream is advantageously configured as planar transmission line to transition from 50 ohm at the transmitter and receiver (microstrip line or MSL is a preferred embodiment of said planar transmission line) to planar transmission line of sufficiently high impedance, advantageously selected to be 150 ohms as will be detailed in a later paragraph, to produce a line width equal to the diameter of the flow channel, advantageously selected to be in the range 50 to 100 micrometers, as seen in FIG. 8. The transition is advantageously designed as an impedance transformer. Two preferred embodiments are shown: one for single frequency operation with narrow bandwidth but better match; for example, a 5 step quarter wave structure with Chebychev coefficients as shown in FIG. 6. Alternatively, multiple frequency use requires greater bandwidth at the expense of match; for example, a continuous exponential taper from 50 ohms to the needed higher impedance shown in FIG. 7. The cells in the flow channel are closely coupled to the otherwise open circuited final segment of the MSL via near field and fringe field coupling, as seen in FIG. 8, wherein the cells are Rayleigh scatterers.

DETAILED DESCRIPTION OF THE DRAWINGS

Figure 1:
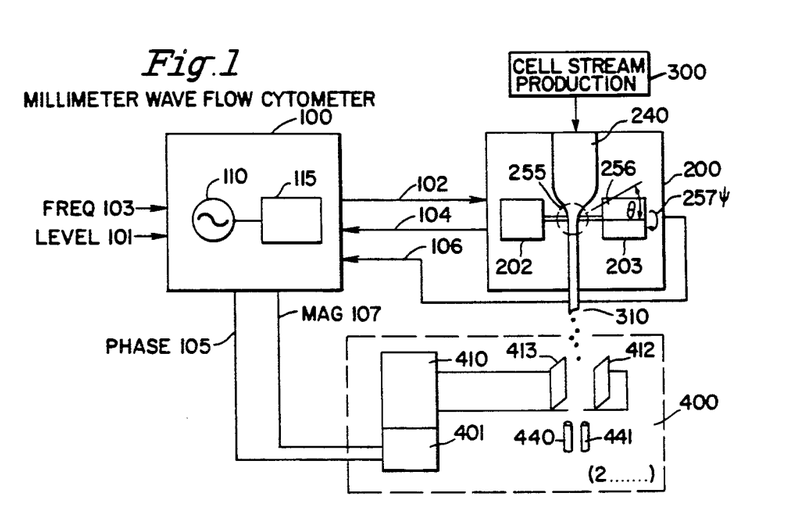

Fig one is a functional block diagram of the system. Four subsystems are shown: the millimetric wave dielectric spectrometer 100 the cellular interface 200; means for production of the cell stream 300; and the cell sorter 400. The spectrometer is comprised of a stabilized millimeter wave source 110 with selection of at least one of a plurality of frequencies and ratiometric phase/amplitude receiver 115. The unicellular interface 200 is preferably comprised of microstrip line transitions 202 and 203 at port one and port two, respectively that allow interaction between the millimeter wave fields (generated as well as received for scattering parameter analysis by 100) and the cell stream 240 at interaction zone 255. Magnitude 107 and phase 105 outputs of ratiometric receiver 115 represent scattering parameter $S_{11}$ if forward power sample 102 is used to reference reflected power 104 whereas magnitude and phase $S_{21}$ is represented if forward power sample 102 is used to reference a bistatic power sample 106 illustrated as forward scattered power wave. Bistatic data are collected as a function of scattering angle theta, 256, for copolarized and cross polarized, angle phi, positions 257 of transition 203, frequency 103 and power level 101, only the last three apply to monostatic (reflection) scattering parameters. The cell sorter 400 is comprised of electronic logic 401 comprised of timers, logic gates, delay lines, comparitors and so forth as applied to the scattering parameter data taken from cell stream to drive deflection plates 412 and 413 in accordance with statistical decision alorithms based on learning machines that make use of a parametric description of at least two reference groups with at least one descision boundary to separate known cell types and functional status whereby new samples are classified into one of said reference groups. For a complete discussion of pattern recognition techniques using such signal processing to classify specimens according to reference groups, see Nilsson, N. J. [1966]which is incorporated herein by reference. Nozzle 310 pumped at an ultra sonic frequency, typically in the $10^4$ Hz range, to convert the charged cell stream into charged droplets in air which are acted upon by electrostatic deflection plates 412 and 413 for sorting into collection vessels 440, 441 etc as disclosed by Bonner, [U.S. Pat. No. 3,826,364].

Figure 2:
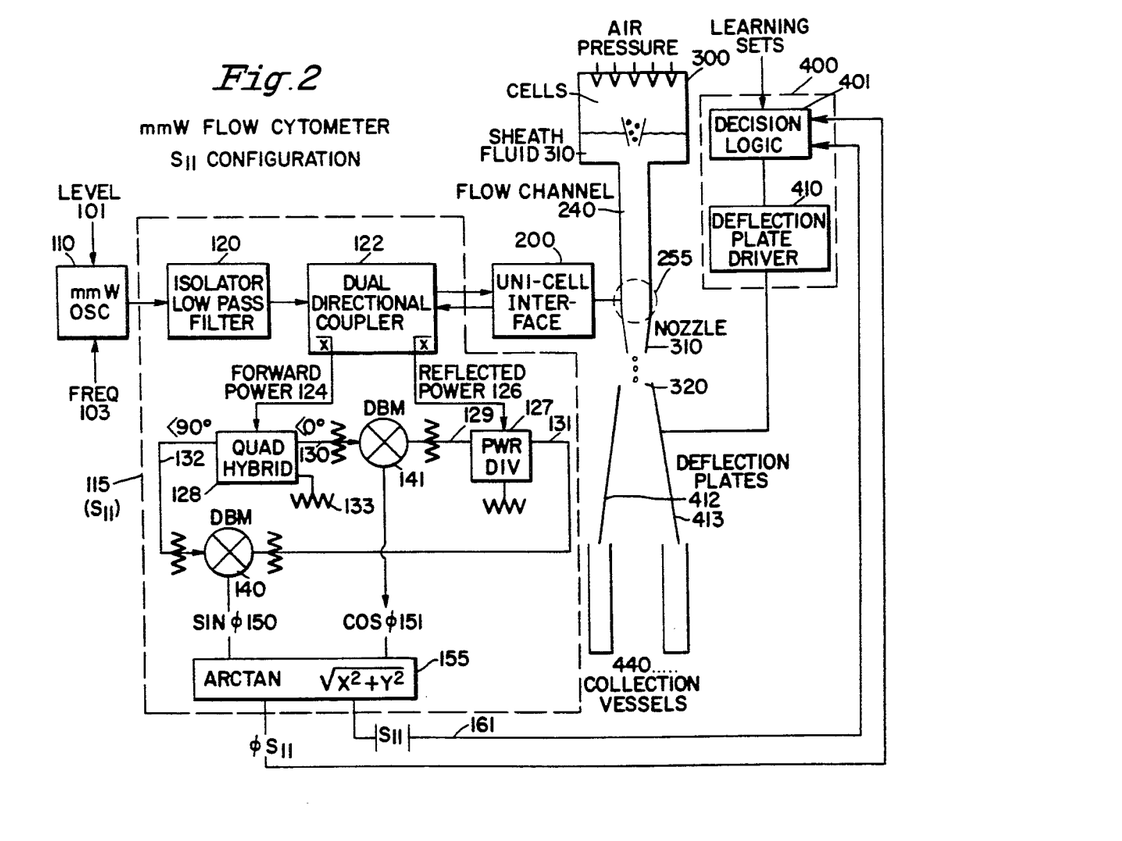
FIG. 2 is a functional diagram of the reflection mode (monostatic, i.e. scattering angle zero or scattering parameter $S_{11}$) configuration of the millimetric wave dielectric spectrometer.

Fig two is a functional block diagram of the reflection mode ($S_{11}$) of operation. Millimeter wave generation components of fig one are not repeated except to note that the stable millimeter wave oscillator 110 in FIG. 1, is advantageously connected to a isolator and low pass filter 120 to prevent oscillator pulling and spurious responses, respectively, in the scattering parameter instrumentation. Samples of incident power waves and reflected power waves become the reference and test channels of the complex ratiometer. That is, a dual directional coupler 122 samples power incident upon the cell stream (known as forward power, 124) via transition 202 of interface 200; and the power reflected 126 by the cell stream also reaches coupler 122 via transition 202 of interface 200. T h e preferred embodiment of the complex ratiometer makes use of the sample of forward power, 124, as one input to quadrature hybrid 128 which produces, in turn, two outputs, 130 and 132, related to the input as half power at zero and 90 degrees phase shift, respectively. The fourth port of quadrature hybrid 128 is terminated by matched load 133. The reflected power, 126, is input to power divider 127 which produces in turn two outputs, 129 and 131, each at half power but without phase shift with respect to the input. Two double balanced mixers (DBM) 140 and 141 use the reflected power 129 and 131 from divider 127 as input to the mixer RF ports; where as the zero and 90 degree phase shifted versions of the forward power, 130 and 132, become inputs to the local oscillator (LO) ports of the mixers 140 and 141, respectively. Attenuators set the LO level 10 dB higher than the RF level (advantageously set to 10 dBm and 0 dBm, respectively) to insure proper operation of the DBM as phase detectors. The intermediate frequency (IF) is DC coupled to provide levels proportional to the sine 150 and cosine 151 of the phase angle theta between the forward 124 and reflected 126 power. These become input to a signal processor 155 that computes the arctangent of the sine and cosine to produce the phase angle 160 of $S_{11}$; and the square root of the sum of squares to produce the magnitude 161 of $S_{11}$. This polar representation of the complex scattering parameter $S_{11}$, is used by decision logic 401 to operate the deflection plate driver 410 of cell sorter 400 in order to deflect cell droplets 320 into their respective collection vessels, 440, 441,...in accordance with the methods disclosed by Bonner et al, [U.S. Pat. No. 3,826,364].

Figure 3:
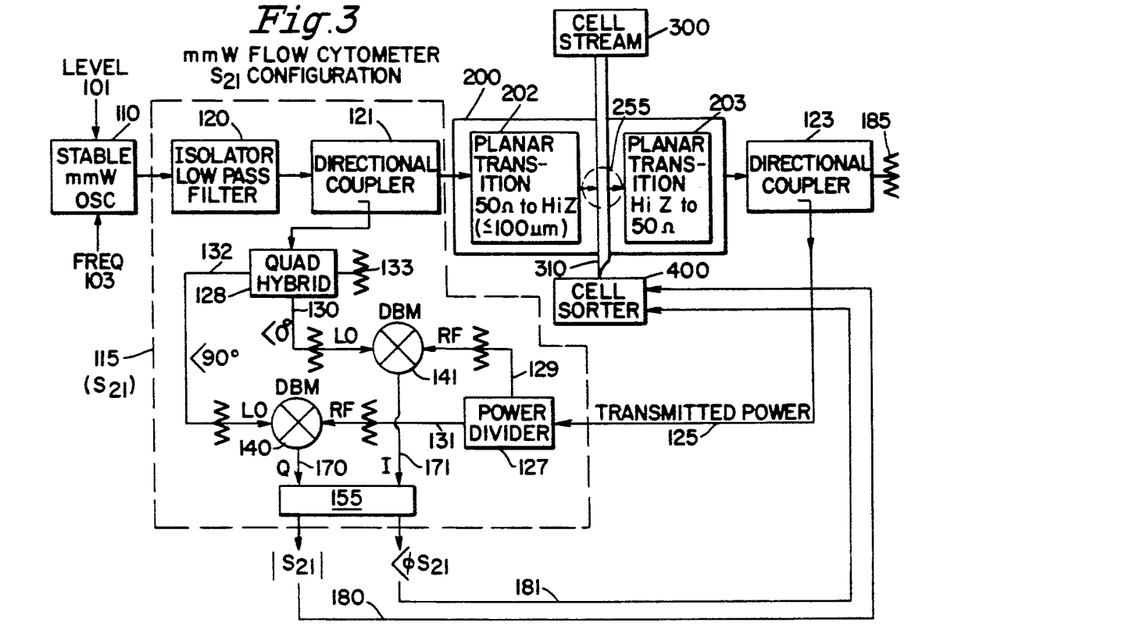
FIG. 3 is a block diagram of the transmission mode (bistatic, eg. scattering angle 180 degrees as one of a plurality of $S_{21}$ configurations) of the spectrometer. Several items are common to both configurations as will be explained in the detailed description to follow. In both cases, a phase/magnitude receiver is used for vector network analysis of $S_{11}$ and/or $S_{21}$.

FIG. 3 is a bistatic (eg. forward scatter case of $S_{21}$) configuration of the millimeter wave spectrometer. The configuration of items 100 through 120 inclusive are the same as for FIG. 2. The dual directional coupler 122 is replaced, however, by two directional couplers that sample incident 121 and transmitted 123 power, respectively. Connection of the quadrature hybrid 128 and its outputs to double balanced mixers 140 and 141 are the same as for fig two. Likewise, the power divider 127 and its outputs 129 and 131 are connected to mixers 141 and 140 as before. The input to power divider 127 is different in this configuration as compared the monostatic case as the transmitted, e.g. forward scattered, power 125 is taken from directional coupler 123. The output of mixers 140 and 141 are also, therefore, different in that they represent the in-phase 171 and in-quadrature 170 components of complex scattering parameter $S_{21}$. Processor 155 still calculates the arctangent and root sum of squares of the rectangular coordinate inputs to yield the magnitude 180 and phase 181 for scattering parameter $S_{21}$.

These become inputs to cell sorter, 400 whose operation is the same as in fig two.

Figure 4:
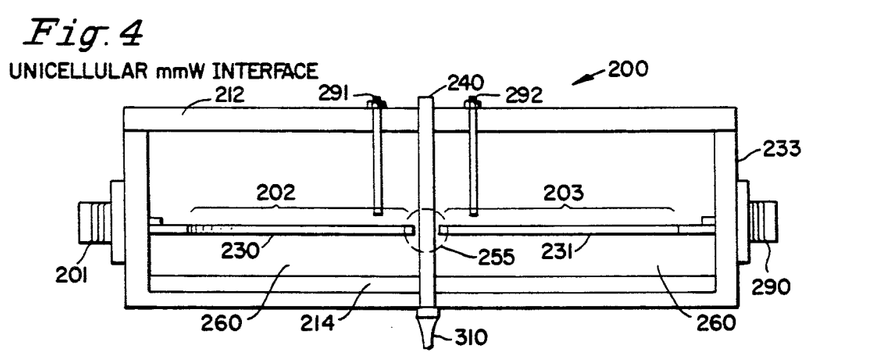

FIG. 4 is the unicellular interface 200 in side (elevation) view. Port one, the input port 201 is preferably configured with 2.4 mm coax to 50 ohm microstrip line (MSL) launcher that ends in a tab, advantageously 20 mil wide, soldered to the 50 ohm input segment 204 of the MSL impedance transformers 202 on substrate, 260. Similar configuration exists for transition 203. The transition preferably matches 50 ohms at the input 204 to the higher impedance at the output 210 needed to reduce the transverse dimension of the final MSL width with the flow chamber 240. The transitions are advantageously tuned to remove residual mismatch for the flow channel filled with electrolyte by means of dielectric posts 291 and 292 positioned over the MSLs and held in place by collets on the lid 212 of the enclosure 233. The ground plane 214 of substrate 260 is in contact with and supported by the bottom of enclosure 233. Lid 212, substrate 260, ground plane 214, and the floor of the enclosure 233, are fenestrated to accept flow channel 240 in a slip fit. Nozzle 270 extends beyond the enclosure for access of electrostatic deflection plates to the droplets so produced as detailed in later drawings.

Figure 5:
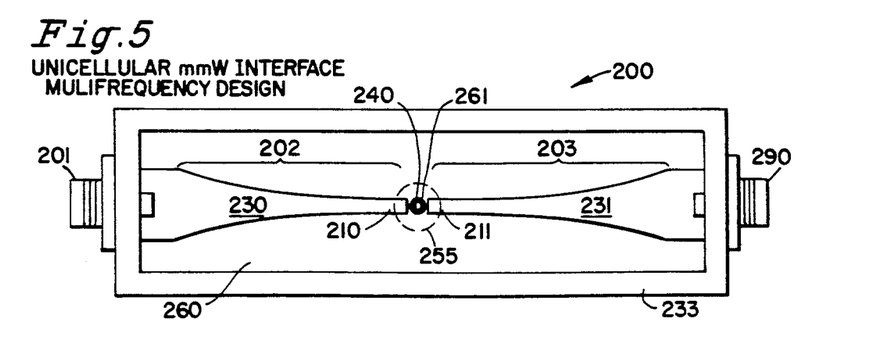

FIG. 5 is a plan view of the cellular interface showing a specific embodiment of the MSL impedance transformers on the substrate 260. In this case, a continuous exponential taper 230 of line width (hence impedance) from 50 ohms at the tab 204 of the coax launcher 201 to the final, higher impedance segment 210 over a distance of 2 wavelengths in the effective dielectric constant of the substrate 260 to produce a low VSWR match over a 20% bandwidth. The final line segment 210 is open circuited at the cell stream channel 240 with wall 261 to create a mismatched termination for the otherwise open circuited final MSL segment. The input transition 202 is repeated in mirror image as transition 203. Transition 203 is illustrated for the forward scatter direction towards port two and coax MSL launcher 290 via taper 231 wherein initial MSL segment 211, taper 231 and launch segmetn are the mirror image of terminal segment 210, taper 230, and launch segment 204 of transition 202 connected to port one via coax connector 201. In the bistatic case, incident power is sampled by the forward power arm of dual directional coupler 122 in combination with transition 202 whereas scattered power is sampled by transition 203 and directional coupler 123. If only monostatic scattering parameter measurements are made transition 203 is terminated in a matched load and transition 202 serves for both incident and reflected power sampling via dual directional coupler 122 per FIGS. 2 and 3. The preferred embodiment is a substrate 260 of dielectric constant of 25, and substrate height of 50 mils, and a conductor 0.0014 mil thick. In this case, the final impedance needed to produce a line width equal to a flow channel diameter of 100 microns is a nominal 150 ohms; thus, the 2 wavelength length of the tapered transition is 2(7.5/SQR 14) or 8 mm long for a 40 GHz center frequency. Line widths and impedances are calculated by the methods described in Hoffman [1987]which is hereby incorporated by reference.

Figure 6:
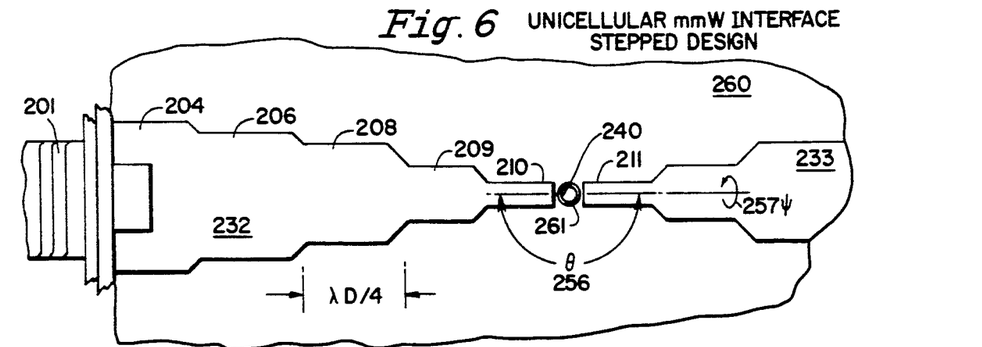

In reference now to FIG. 6, the transition may alternatively be of the multistep quarter wave type for low VSWR at a narrow band, e.g. 5% bandwidth, of operation as shown in another preferred embodiment 232 shown only for port one where it is understood that the mirror image 233 leads to port two as described for the preceeding figure. Here impedance steps 204, 206, 208, 209 are selected by Chebychev polynomial. The preferred embodiment further employs a substrate 260 of dielectric constant 25, a substrate height of 50 mils, and a conductor 0.0014 mil thick. In this case, the final segment 210 connected to port one and the initial segment 211 connected to port two are of high impedance needed to produce a line width equal to a flow channel diameter, that is, 100 microns line width for a nominal 150 ohms in the preferred embodiment. The impedance steps for minimal reflections from said beginning to said ending impedances are 50, 54.7, 71.7, 104.7, 136.9, and 150 ohms as in Young [1962]which is hereby incorporated by reference. The effective dielectric constant is ca 14; thus, the length of each 5 quarter wave steps needed for such a transition is about 2.5 mm for a total transition length of 12.5 mm. The line widths to accomplish the specified impedance in such a stepped transformer are calculated as in Hoffman [1987]according to well established methods.

Figure 7:
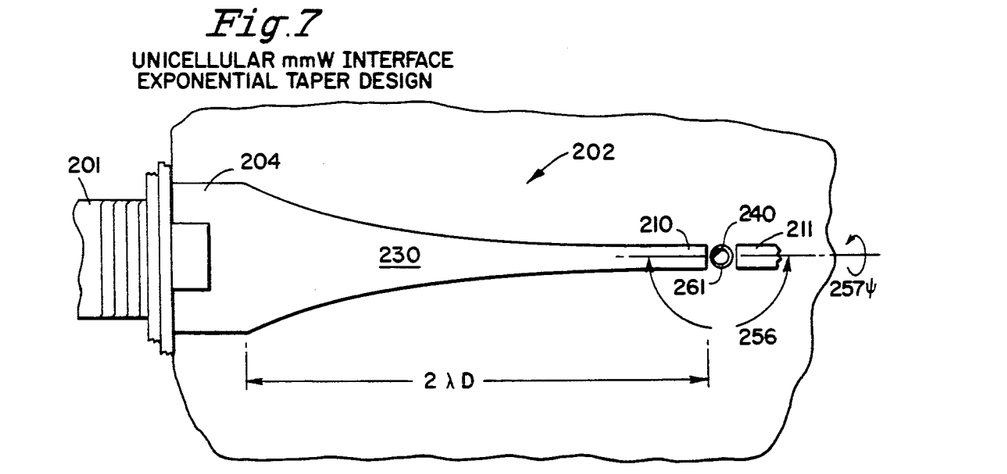

In reference now to FIG. 7 where the tapered impedance transformer is illustrated in plan view, note that both the tapered and stepped impedance transformers begin with 50 ohms in segment 204 and end with 150 ohms in segment 210 in the preferred embodiments, but differ in the intermediate ranges. This is a consequence of increased bandwidth. In either case, port one leads from MSL launcher 201 to the open circuited line segment 210 for incident power waves; and both use mirror image transitions from initial segment 211 to port two MSL launcher 290. Both have at least two degrees of freedom in orientation of the bistatic portion connected to port two: One plane of motion is within the plan view pivoted about an axis centered on the cell stream to sample scattering angle theta, 256, whereas another axis of rotation, angle phi, 257 is centered about the axis of port one, i.e. angle phi is one of parallel and perpendicular to polarization of the incident power wave, wherein the incident polarization is advantageously parallel to the long axis of the cell stream. Only the copolarized and 180 degree selections for polarization and scattering angle, respectively are illustrated.

Figure 8:
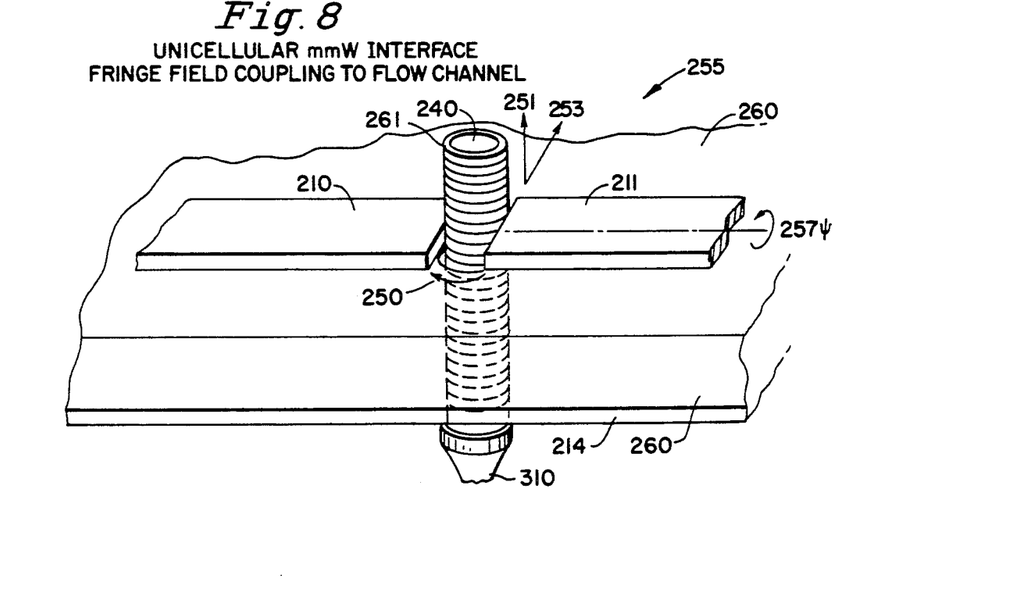

As illustrated in FIG. 8, flow channel 240 and wall 261 are in the near field of the otherwise open circuited final segment (s), 210 and 211, of the MSL impedance transformer at the high impedance end of cell interface 200. Fringe fields 250 at the high impedance end serve to couple input port 201 of the cell interface to the cell stream channel 240. Both tangential 253 and normal 251 field components associated with the final segment(s) 210 and 211 of the MSL transition are involved. A mirror image impedance transformer leads port two 290 of the cellular interface to the interaction zone. In the case of reflection mode operation, output port 290 is advantageously terminated in matched load 185.

In the case of forward scatter, i.e. transmission, operation, a second transition from 150 ohms back to 50 ohms in mirror image to the input side, senses the forward scattered field by fringe field 250 coupling into its 150 ohm segment, 211, thence to port two, 290, and into directional coupler 123, the main line of which is now terminated with the matched load represented by the receiver test channel input; alternatively, the receiver may be connected to the coupled arm as illustrated with another matched termination at the main line.

Use of the System

The basic operational parameters of the instant invention are choice of carrier frequency, scattering angle, polarization, and power level. The choice of carrier frequency is based on the fact that scattering cross section is proportional to the 4th power of frequency for a Rayleigh scatterer. Thus, a higher center frequency and a broader sweep range will improve target detection and discrimination for fixed incident power. However, construction of the apparatus and cost of millimeter wave components increase with operating frequency. The choice of scattering angle is based on the fact that forward scatter cross sections for Rayleigh scatters is larger and better behaved with respect to frequency dependency than is back scatter. Other scattering angles and depolarization power are useful to estimate target asymmetry. The choice of incident power level is limited at the upper end by the need to avoid substantial heating of the cell stream. A generally acceptable temperature elevation is 1/10 degree Centigrade, but this is not likely to be a problem due to the relatively high flow rate in the interaction zone that is needed to accomplish hydrodynamic focusing. A more pertinent operational constraint is the need to keep the signal levels on the double balanced mixer diodes of the ratiometric receiver in the square law region. Generally, this is in the range $-10$ to $-40$ dBm. This range is set not only by the incident power level, but any amplifiers, pads, dividers, couplers and so forth prior to detection as is well known to those skilled in the art of receiver design. The incident power level may not be so low as to produce scattered power waves that are below the level of detectability by the ratiometric receiver when maximum gain and minimum attenuation is selected.

The basis of operation for the unicellular interface is a very narrow, planar transmission line coupled via its near field into a cell stream composed of Rayleigh scatters. The preferred embodiment of the planar transmission line is microstrip line (MSL), the final segment of which is open circuited in close proximity to the cell stream channel. The microstrip line (MSL) must be of sufficiently high impedance to result in a line width no greater than the outer diameter of the thin wall, cell stream channel (maximum diameter of 100 microns). The inner diameter of the cell channel is determined by the wall thickness, normally 10–20 microns. The cells flow past the interaction region, 255, in single file by virtue of hydrodynamic focusing as described by the Kachel and Menke chapter of the Melamed et al book [1979]which is hereby incorporated by reference.

The width of the MSL is also dependant upon the thickness of the conductor, the dielectric constant of the substrate, and the ratio of the distance of the conductor from the ground plane by the distance of the lid from the ground plane. In order to insure interaction with the cell stream, it is advantageous to specify a channel wall thickness in the range 10 to 20 microns and to tailor the radius of the fluid sheath layer as the millimeter wave beam cannot be confined to a spot[1] appreciably smaller than ½ wave length in the effective dielectric constant of the terminal (i.e. high impedance) segment of the cellular interface. The MSL substrate dielectric constant is selected to be near that of water at the frequency of operation. In the case of Ka band, substrate relative dielectric constant is preferably $e'=25$. Further design parameters of the preferred embodiment are MSL width of 100 microns, substrate thickness of 1.4 mils, substrate height of 50 mils, height to the lid of 5000 mils; thus for $e'=25$, $e'_{eff}=14$ and $Z=150$ ohms. Since the dimensions are both small and critical, the dielectric material is preferably ceramic. This also insures a concentric fit for the cell stream channel drilled (ultrasonically) through the substrate at the end of the narrow, high impedance end that is otherwise open circuited transmission line.

1 The beam optics would be Gaussian. A spot then becomes a waist of narrowed beam width.

At least one dielectric post located over the MSL are used to reduce any residual mismatch in the impedance transformer when the flow channel is filled with electrolyte alone. The penetration and position of the post is adjusted to minimize residual mismatch In this way, the cell stream constitutes a mismatched (with respect to electrolyte alone) termination of the final, high impedance, MSL segment.

In the reflection mode of operation, port 2 is terminated. The directional coupler operantly connected to the input transition serves to couple the incident power via its main line into the first transition whereas its coupled arms serve to sample the forward and reflected power which are applied to the matched load represented by the reference and test channels of the complex ratiometric receiver, respectively. In the transmission mode of operation, the input transition is repeated in mirror image in the forward scatter direction for insertion loss measurements via a second directional coupler with its main line terminated by the matched load represented by the test channel input of the complex ratiometric receiver. Furthermore, a plurality of scattering angles other than 0 and 180 degrees are accomplished by rotation of the input and output port axes with respect to the plane of intersection of the cell interface with the flow channel for angles other than 0 and 180 may map additional scattering angles. Likewise, rotation of the second transition about its own axis to an orientation orthogonal to the axis of the input transition measures the depolarization power of the cell stream at each frequency and scattering angle selected.

The residual mismatch of the unicellular interface described above and in FIG. 4 may be numerically compensated by means of circuit standards, time domain reflectometry and deimbedding of the test fixture, as is well known to those skilled in the art of vector network analysis [Ulriksson, 1981]. In the case of reflection mode operation, the two standards are a matched load and a short circuit to establish the location of the reference plane. These are implemented in place of the cell stream channel via the 100 micron hole in the substrate by means of a micro manipulator. The calibration device is a metalized version of the cell channel to make a 150 ohm load with a tab to contact the line and ground plane. The calibration short is a solid metal pin and tab to contact the line and the ground plane In the transmission line case, an additional standard is needed to complete a "through" connection across the space normally occupied by the cell stream channel In any case, it is noteworthy that relative measurements of the complex scattering parameters may be made on the cell suspension medium without cells for comparison to the electrolyte with cells. Since the dielectric properties of physiological electrolyte solutions are well known, the dielectric properties of the cells may be inferred by a lumped capacitor model as used by Larsen and Jacobi [U.S. Pat. No. 4,240,027] at HF band frequencies.

Since the cell stream represents Rayleigh scatters, it is instructive to emphasize the distinction between detection and resolution. It is obvious that a millimeter wave system, even given the wavelength contraction by a factor of 5 due to the substrate dielectric constant of 25, cannot resolve two targets only tens of microns in diameter. The fact that the cell stream is hydrodynamically focused, as per Kachel and Menke [1979]to produce single file cells is critical to the operation of the system since two individual scatters cannot be separately resolved. On the other hand, bulk properties are not used as was the case with Larsen et al 1978.

As noted in prior paragraphs, each cell is a Raleigh scatterer. As is well known, this regime has a fourth power of the frequency dependance between wave number and scattering cross section. This means that a 20% increase in frequency offers a factor of 2 increase in scattering cross section. If, for example, the cells flow by the interaction region at 1 meter/sec and the interaction region is a cylinder 1.2 mm long (i.e. equal to the height of the MSL substrate) and 1/10 mm diameter (equal to the outer diameter of the flow channel), then the cells are in the interaction region for about 1 msec. This is more than sufficient time for the millimeter wave source to step or sweep several frequencies. Then slope of $|S_{11}|$ and the slope of $|S_{21}|$ as a function of frequency improves the estimation of cell size in comparison to a single frequency. Similarly, depolarization power as a function of frequency improves upon that at a single frequency to estimate cell shape.

Finally, the interaction mechanism is of some interest. If the cell stream were in the far field of a radiator, eg a patch antenna, the scattering cross section would be about $4.2 \times 10^{-5}$ or $-44$ dB re to the limiting high frequency value. This is a difficult, though not impossible, detection problem. Unpublished results by Larsen at 4 GHz, i.e. ten times lower frequency, showed near field direction of a $\frac{1}{2}$ mm nylon cylinder with a wave length in the coupling dielectric of about 8.1 mm. The calculated scattering cross section in that case was $1.3 \times 10^{-3}$ ($-29$ dB re to high frequency limit) yet the target was detected with a signal to noise ratio of better than 20 dB at the electric field peak of the aperture field distribution. This unexpected result suggests that when the target is in the near field of the radiator, the target modifies the local characteristic impedance of the transmission lime. In other words, the interaction mechanism appears to be modeled as a mismatched termination. This model explains the vast improvement in detectability over that predicted by far field scattering cross section.

What is claimed is:

1. Apparatus for microwave flow cytometry, comprising:
    (a) Means to isolate cells in a fluid and to hydrodynamically focus said cells single-file through an interaction zone of dimension comparable to a single cell;
    (b) Generating means to generate, direct and closely couple incident microwave energy of predetermined frequency and polarization into said interaction zone;
    (c) Receiving means to receive waves closely coupled to said interaction zone which have been affected by a cell in said interaction zone, with at least one of said generating or receiving means being rotated in at least a first plane;
    (d) Measuring means to read values from said generating and receiving means, said measuring means evaluating complex S-parameters of each cell in said interaction zone as a function of frequency and as a function of the angular displacements of the rotated means in at least said first plane;
    (e) Processing means receiving data from said measuring means, said data being used to classify cells in said interaction zone as member of a plurality of reference groups, said reference groups being predefined by prior tests upon known samples.

2. Apparatus as defined in claim 1, wherein the rotated means are mechanically rotated around an axis perpendicular to the axis or the cell motion in the interaction zone.

3. Apparatus as defined in claim 1, wherein the rotated means are mechanically rotated around an axis parallel to the axis of cell motion in the interaction zone.

4. Apparatus in claim 1, wherein said means being mechanically rotated is the receiving means.

5. Apparatus as in claim 1, wherein said prior tests of known samples are executed using a minimum number of both normal and pathological specimens in said fluid to characterize said reference groups.

6. Apparatus in claim 1, wherein the receiving means detects predominantly that portion of the incident wave reflected by each cell in the interaction zone.

7. Apparatus in claim 1, where the receiving means detects predominantly that portion of the incident wave transmitted by each cell in the interaction zone.

8. Apparatus as defined in claim 1, wherein said interaction zone is comprised of a flow channel and said generating or receiving means include transmission lines which are closely coupled to said interaction zone.

9. A method of cytometric evaluation of isolated cells, comprising the steps of:
   (a) Isolating said cells in a fluid and hydrodynamically focusing said cells single-file in an interaction zone of dimensions comparable to a single cell;
   (b) Generating and closely coupling incident microwave energy of a predetermined frequency into said interaction zone;
   (c) Receiving closely coupled waves affected by each cell in the interaction zone while mechanically rotating at least one of the generating or receiving wave directions in at least one plane;
   (d) Measuring at least one complex S-parameter based on readings from the generated and received values as a function of frequency and as a function of the angular position for said mechanical rotation;
   (e) Processing data generated during said measuring step to classify each cell under analysis as a member of one of predetermined reference groups, said reference groups being previously defined by applying measuring steps to known calibrating samples of cells and fluids.

* * * * *